United States Patent
Farr et al.

(10) Patent No.: US 10,084,278 B2
(45) Date of Patent: Sep. 25, 2018

(54) IMPLANTABLE LEAD ASSEMBLY

(71) Applicant: PACESETTER, INC., Sylmar, CA (US)

(72) Inventors: Alexander Farr, Woodland Hills, CA (US); Steven R. Conger, Agua Dulce, CA (US); Keith Victorine, Santa Clarita, CA (US); Sean Matthew Desmond, Moorpark, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 15/716,131

(22) Filed: Sep. 26, 2017

(65) Prior Publication Data
US 2018/0019562 A1 Jan. 18, 2018

Related U.S. Application Data

(62) Division of application No. 14/681,985, filed on Apr. 8, 2015, now Pat. No. 9,800,010.

(51) Int. Cl.
| | |
|---|---|
| *A61N 1/00* | (2006.01) |
| *H01R 43/16* | (2006.01) |
| *A61N 1/375* | (2006.01) |
| *A61N 1/05* | (2006.01) |
| *A61N 1/362* | (2006.01) |

(52) U.S. Cl.
CPC .......... *H01R 43/16* (2013.01); *A61N 1/0563* (2013.01); *A61N 1/3622* (2013.01); *A61N 1/3754* (2013.01)

(58) Field of Classification Search
CPC .................................... A61N 1/0587
USPC .................................. 607/122, 127
See application file for complete search history.

*Primary Examiner* — Nadia A Mahmood

(57) ABSTRACT

An implantable lead assembly is provided that comprises a lead body having a proximal end portion and a distal end portion, and having a length extending there between. A plurality of electrodes are disposed along the lead body. A plurality of cable conductors are contained within the lead body, the conductors extending from the electrodes to the proximal end portion. A lead connector is provided at the proximal end portion. The lead connector includes a connector pin configured to mate with a corresponding header contact; a first termination pin coupled to one of the plurality of cable conductors; a collar coupler securely and electrically coupling the connector pin and first termination pin in an axially offset alignment with one another; and a body segment that is elongated along a longitudinal axis and extends between a header mating face and a lead mating end. The body segment is over-molded about the connector pin, the first termination pin and the collar coupler, the connector pin extending from the header mating face, the first termination pin extending from the lead mating end.

8 Claims, 10 Drawing Sheets

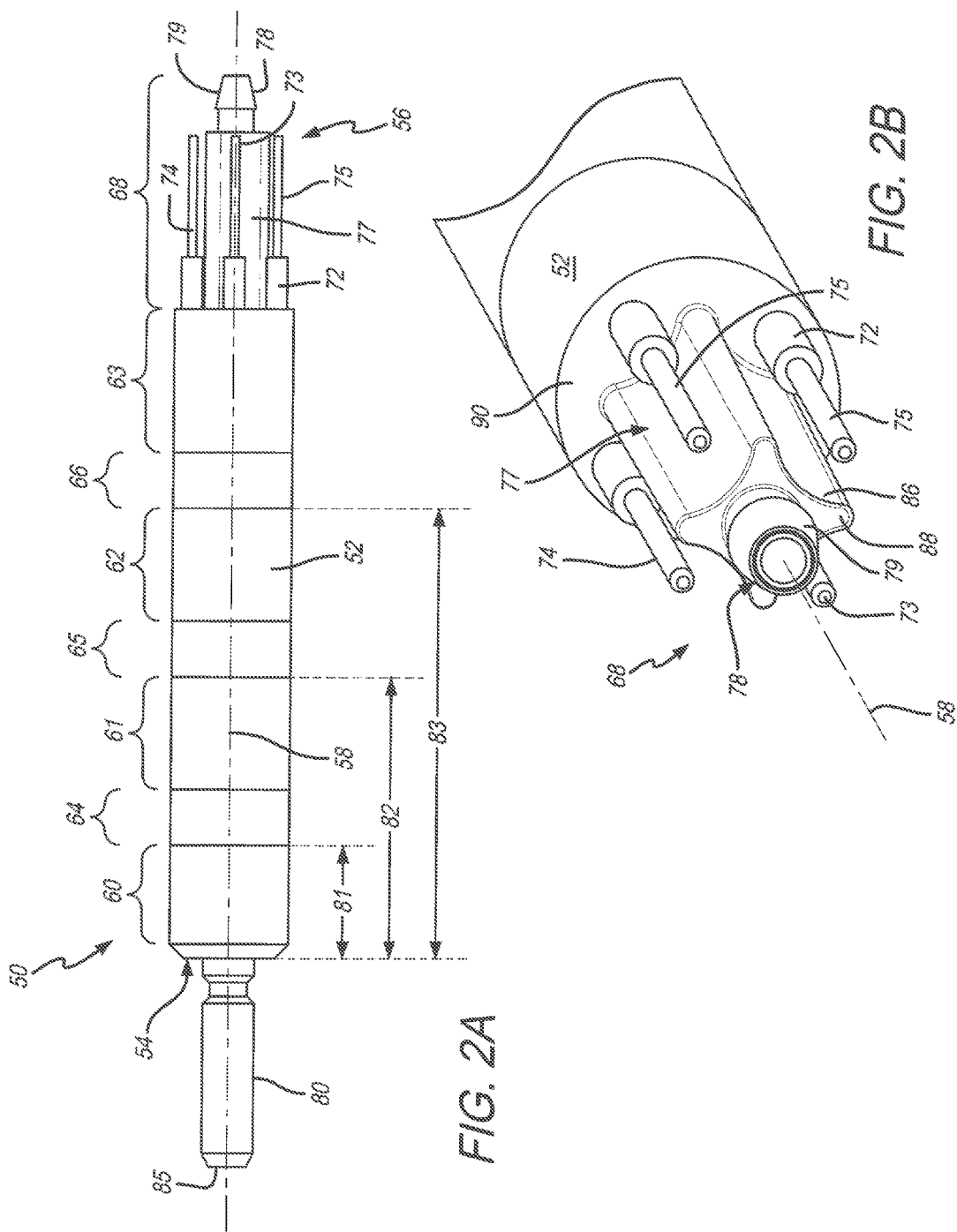

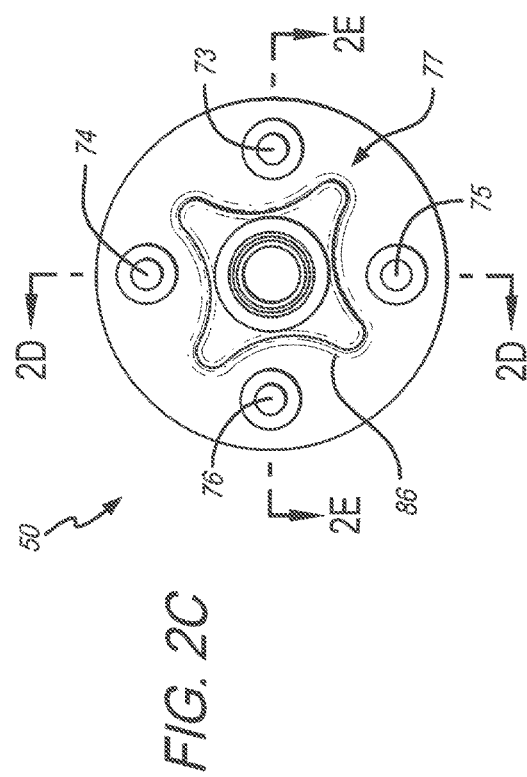
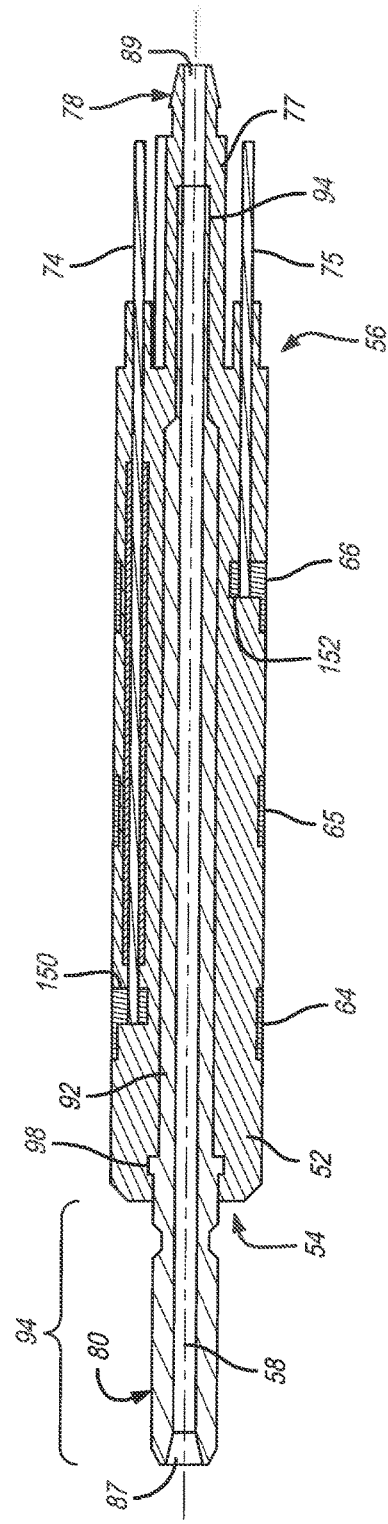
FIG. 2C
FIG. 2D

IMPLANTABLE LEAD ASSEMBLY

CROSS REFERENCE TO RELATED APPLICATIONS

This application is a divisional of U.S. patent application Ser. No. 14/681,985, filed Apr. 8, 2015.

FIELD OF THE INVENTION

Embodiments herein generally relate to implantable lead assemblies, and more particularly to implantable lead assemblies having an over-molded connector assembly.

BACKGROUND OF THE INVENTION

A body implantable lead assembly forms an electrical connection between a patient's anatomy and a pulse generator such as a cardiac pacemaker, an implantable cardioverter defibrillator (ICD), an appetite or pain suppression device, and the like. The lead assembly includes a lead body comprising a tubular, flexible biocompatible, biostable insulative sheath or housing, such as formed of silicone rubber, polyurethane or other suitable polymer. One example of a lead body is a lead having a tip electrode, a ring electrode and one or more other electrodes disposed along the lead body. In many configurations, the lead includes a coaxial conductor extending about a central lumen of the lead body. Another example of a lead body is a cardioverter/defibrillator lead that includes a sensing ring, a shocking right ventricle (RV) electrode, a shocking superior vena cava (SVC) electrode and a tip sensing/pacing electrode. The lead includes a multi-lumen housing, each lumen of which carries a separate conductor through the lead housing to each of the sensing ring, RV electrode, SVC electrode and tip electrode.

In certain applications, coil conductors may be used, while in other applications single or multi-strand cable conductors may be used to connect the pulse generator at the proximal end portion of the lead with the corresponding electrodes at the distal end portion of the lead. In some existing multi-lumen lead bodies, a combination of a coil conductor and one or more cable conductors may be utilized.

To facilitate connection of an implantable lead to a compatible pulse generator, the proximal lead connector is inserted and secured in the device header. This provides the mechanical and electrical connection between the implantable lead and the device. For the current generation cardiac leads, the design includes a connector pin which is terminated to an inner coil conductor by welding and/or crimping. The coil conductor extends from the connector to the distal tip of the lead.

Current generation IS4/DF4 leads utilize a coil conductor (extending about the core lumen) to connect the tip electrode to the connector pin and utilize cables to make additional terminations. Termination crimp sleeves are attached to the proximal end of each conductor cable. The termination crimp sleeves are welded to termination pins on the distal end of conventional IS4/DF4 connectors to provide an electrical and mechanical connection. The IS4/DF4 connectors have three distal termination pins to facilitate connection with three termination crimp sleeves and cable assemblies. The IS4/DF4 leads utilize an inner conductive coil to provide an electrical connection from the connector pin to the lead tip electrode. In active fixation leads, the conductive coil is also used to provide torque through rotation of the connector pin to extend and retract the helix fixation mechanism. In passive fixation leads, the conductive coil acts as an electrical conductor and as a pathway for delivery tools (such as guidewires and stylets).

However, existing connector assemblies used with the above noted lead configurations experience certain limitations. For example, the connector pin, which is rotatably located in a header mating face of the connector assembly, exhibits a certain amount of axial movement The axial movement of the connector pin affects the position of the connector within the header which changes the relative alignment between contacts on the connector assembly relative to mating contacts in the header. The axial movement of the connector pin limits manufacturing tolerances associated with other contacts on the connector assembly.

A need remains for a connector assembly for a lead body comprising multiple cable conductors wound in a spiral manner about the lead body without an inner coil conductor to provide select characteristics in lead delivery and lead body durability.

BRIEF DESCRIPTION OF THE INVENTION

In accordance with at least one embodiment, an implantable lead assembly is provided that comprises a lead body having a proximal end portion and a distal end portion, and having a length extending there between. A plurality of electrodes are disposed along the lead body. A plurality of cable conductors are contained within the lead body, the conductors extending from the electrodes to the proximal end portion. A lead connector is provided at the proximal end portion. The lead connector includes a connector pin configured to mate with a corresponding header contact; a first termination pin coupled to one of the plurality of cable conductors; a collar coupler securely and electrically coupling the connector pin and first termination pin in an axially offset alignment with one another; and a body segment that is elongated along a longitudinal axis and extends between a header mating face and a lead mating end. The body segment is over-molded about the connector pin, the first termination pin and the collar coupler, the connector pin extending from the header mating face, the first termination pin extending from the lead mating end.

Optionally, the connector pin may be aligned with and extend along the longitudinal axis of the body segment and the first termination pin may be offset radially from the longitudinal axis. The first termination pin is electrically coupled to one of the cable conductors. The cable conductors wind in a spiral manner about a length of the lead body. Optionally, the lead assembly further comprises a second termination pin connected to a ring contact, where the second termination pin extends from the lead mating end. A ring contact extends about an exterior of the body segment at a predetermined position along the body segment spaced relative to the connector pin.

Optionally, a plurality of termination pins extend from the lead mating end. Optionally, the plurality of termination pins include the first termination pin, where the plurality of termination pins extend in a common direction as the longitudinal axis, and the plurality of termination pins are radially distributed outward from the longitudinal axis in a circumferential arrangement about the lead mating end. The connector pin may include a base section that is rigidly secured during molding within the body segment and includes an interconnect section that extends from the header mating face. The connector pin includes an inner end that is over-molded within the body segment, the inner end being physically separated from the conductors. Optionally, the body segment includes a lead interconnect region at the lead mating end, the lead interconnect region having a fluted cross-section to form crimp pockets, the conductors being joined through crimp sleeves to corresponding termination pins in the crimp pockets.

Optionally, the body segment further comprises a support arm and core post projecting from lead mating end and centered along the longitudinal axis, the core post including a flared barb, the core post and barb shaped and dimensioned to be frictionally secured within a core lumen within a proximal end portion of the lead body.

In accordance with at least one embodiment, a method of manufacturing a lead assembly comprises providing a lead connector by: coupling a connector pin to a first termination pin through a collar coupler such that the connector pin and first termination pin are in an axially offset alignment with one another; and over molding a body segment about the connector pin, the first termination pin and the collar coupler, the body segment being elongated along a longitudinal axis and extending between a header mating face and a lead mating end, the connector pin positioned along the longitudinal axis and extending from the header mating face, the first termination pin positioned axially offset from the longitudinal axis and extending from the lead mating end. The method includes attaching the lead connector to a proximal end portion of a lead body having a plurality of electrodes disposed along the lead body, the lead body including a plurality of cable conductors; and joining the first termination pin to a proximal end of a first conductor from the plurality of cable conductors.

In accordance with at least one embodiment, the method further comprises affixing the connector pin within the body segment in a non-rotational manner, and electrically coupling the connector pin to the first conductor by attaching the first conductor to the first termination pin through a crimp sleeve, the cable conductors winding in a spiral manner about a length of the lead body.

In accordance with at least one embodiment, the method further comprises coupling a plurality of termination pins to ring contacts; loading the plurality of termination pins, the ring contacts, the first termination pin, and the connector pin into an injection mold; and over molding the plurality of termination pins, the ring contacts, the first termination pin, and the connector pin such that the plurality of termination pins project from the lead mating end and the ring contacts extend circumferentially about an exterior of the body segment at predetermined positions spaced along the body segment.

In accordance with at least one embodiment, the method further comprises spacing the ring contacts along a length of the body segment by a spacing relative to the header mating face of the body segment. Optionally, the plurality of termination pins and the first termination pin extend in a common direction as the longitudinal axis and are radially distributed outward from the longitudinal axis in a circumferential arrangement about the lead mating end. Optionally, the connector pin includes a base section that is tapered along a length thereof and is rigidly secured during molding within the body segment. The body segment includes a lead interconnect region extending from the lead mating end, the lead interconnect region having a fluted cross-section to form crimp pockets, the conductors being joined through crimp sleeves to corresponding termination pins in the crimp pockets. The body segment may further comprise a support arm and core post projecting from lead mating end and centered along the longitudinal axis, the core post including a flared barb, the core post and barb shaped and dimensioned to be frictionally secured within a core lumen within a proximal end portion of the lead body.

BRIEF DESCRIPTION OF THE DRAWINGS

FIG. 2A illustrates a side view of the connector assembly of FIG. 1B formed in accordance with an embodiment herein.

FIG. 2B illustrates an end perspective view of a lead interconnect region formed in accordance with an embodiment herein.

FIG. 2C illustrates an end view of the connector assembly from the lead mating end formed in accordance with an embodiment herein.

FIG. 2D illustrates a sectional view taken along line 2D-2D in FIG. 2C through the connector assembly.

DETAILED DESCRIPTION OF THE INVENTION

The following description presents embodiments herein. This description is not to be taken in a limiting sense but is made merely for the purpose of describing the general principles of the embodiments whose scope is defined by the appended claims. Although the following embodiments are described principally in the context of cardioverting/defibrillating connector/leads, the present disclosure may be applied to other connector/lead structures. For example, embodiments may be used with devices that suppress an individual's appetite, reduce or offset pain associated with chronic conditions and control motor skills for handicap individuals.

Embodiments herein allow for the design and fabrication of a cardiac lead with multiple conductors within the lead body (e.g., four or more). For example, an IS4 connector assembly is provided herein with four-pin termination hardware and a fluted geometry that allows for the connection of four termination crimp sleeves and cable conductors. Embodiments herein enable the use of a lead with a lead body construction that avoids the use of an inner coil conductor, thereby allowing for select delivery tool interaction and lead body durability. The connector pin is over-molded to prevent rotation (e.g., in connection with a passive fixation lead). By over-molding the connector pin, embodiments herein eliminate axial and radial pin movement, thereby reducing the number of components and manufacturing process steps. To improve lead manufacturability, a feature is present on the distal end of the connector assembly to provide stability during assembly and afford a seal to prevent medical adhesive leakage during backfilling operations. As one example, the connector assembly may be an IS4 compatible lead connector, although numerous other embodiments may be implemented.

Figure 1A:
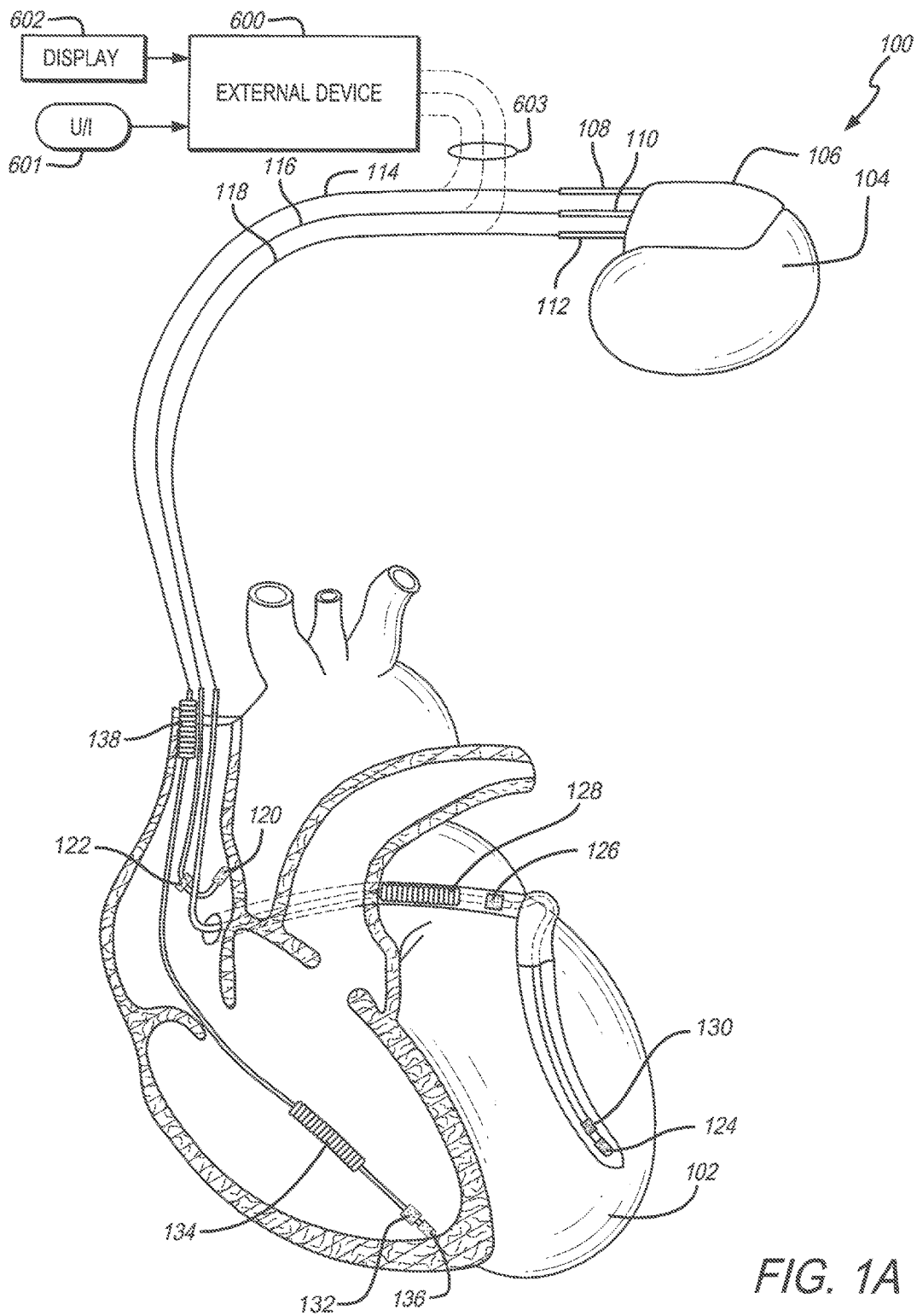
FIG. 1A illustrates an implantable medical device and external device, coupled to a heart in accordance with an embodiment herein.

FIG. 1A illustrates an IMD 100 and external device 600 coupled to a heart 102 in a patient and implemented in accordance with one embodiment. The external device 600 may be a programmer, an external defibrillator, a workstation, a portable computer, a personal digital assistant, a cell phone and the like. The IMD 100 may be a cardiac pacemaker, an ICD, a defibrillator, an ICD coupled with a pacemaker, and the like. The IMD 100 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. The IMD 100 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like.

The IMD 100 includes a housing 104 that is joined to a header assembly 106 that receives connectors 108, 110, 112 connected to a right ventricular lead 114, a right atrial lead 116, and a coronary sinus lead 118, respectively. The leads 114, 116, and 118 measure cardiac signals of the heart 102. The right atrial lead 116 includes an atrial tip electrode 120 and an atrial ring electrode 122. The coronary sinus lead 118 includes a left ventricular tip electrode 124, a left atrial ring electrode 126, and a left atrial coil electrode 128. The coronary sinus lead 118 also includes an LV ring electrode 130 disposed between the LV tip electrode 124 and the left atrial ring electrode 126. The right ventricular lead 114 has an RV tip electrode 136, an RV ring electrode 132, an RV coil electrode 134, and an SVC coil electrode 138. The leads 114, 116, and 118 detect IEGM signals that form an electrical activity indicator of myocardial function over multiple cardiac cycles.

During implantation, the external device 600 may be connected to one or more of the leads 114, 116, 118 through temporary inputs 603. The inputs 603 of the external device 600 receive IEGM signals from the leads 114, 116, 118 during implantation and displays the IEGM signals to the physician on display 622. Optionally, the external device 600 may not be directly connected to the leads 114, 116 and 118. Instead, the IEGM cardiac signals sensed by the leads 114, 116 and 118 may be collected by the IMD 100 and then transmitted wirelessly to the external device 600. Hence, the external device 600 receives the IEGM cardiac signals through telemetry circuit inputs. The physician or another user controls operation of the external device 600 through a user interface 601.

Figure 1B:
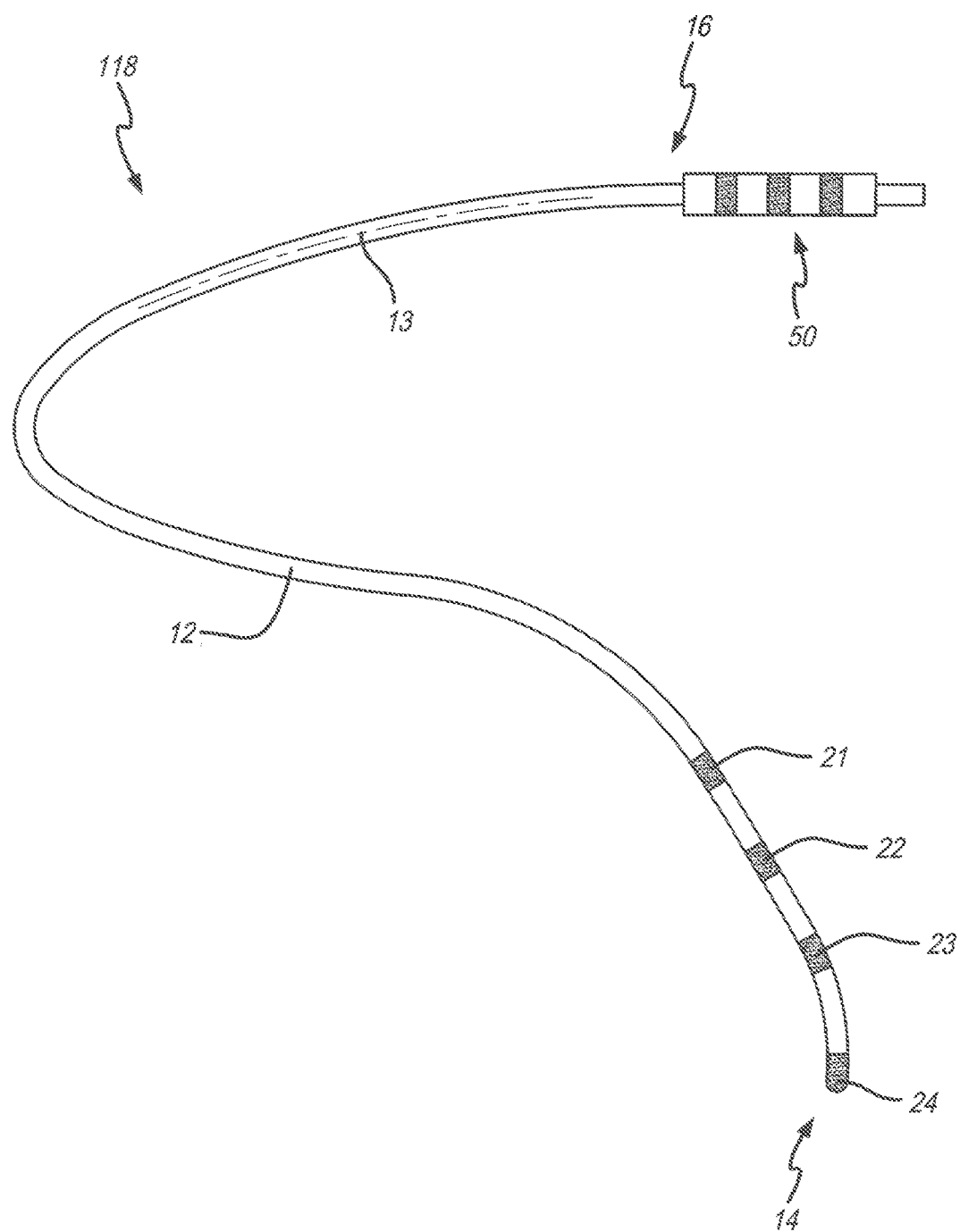
FIG. 1B illustrates a lead assembly formed in accordance with an embodiment herein.

FIG. 1B illustrates the lead assembly 118 formed in accordance with an embodiment herein. The lead assembly 118 includes a lead body 12 having a distal end portion 14 and a proximal end portion 16. The lead body 12 has a length that extends along a longitudinal axis 13 between the distal and proximal end portions 14 and 16. The term longitudinal axis encompasses both linear and non-linear axes. The longitudinal axis 13 of the lead body 12 extends along a curved path that changes as the lead body is flexed, bent and otherwise manipulated. The lead assembly 10 includes a plurality of electrodes 21-24 that may be constructed as tip, coil and/or ring electrodes. The electrodes 21-24 are spaced apart from one another along the lead body, such as proximate to the distal end portion 14. A plurality of conductors (not shown in FIG. 1B) are contained within the lead body 12. The conductors extend from the electrodes 21-25 to the proximal end portion 16. The lead body 12 includes an insulating sheath or housing of a suitable insulative, biocompatible, biostable material such as, for example, silicone rubber or polyurethane, extending substantially the entire length of the lead body and surrounding the conductors. Various combinations of the electrodes 21-24 are used in connection with sensing cardiac signals and/or delivering stimulation therapies.

The proximal end portion 16 is joined to a connector assembly 50 that is configured to couple the lead assembly 118 to an IMD 100, external device 600 or other device. The connector assembly 50 comprises one or more connectors that may conform to the DF-1 standard when used for supplying electrical impulses for defibrillation, and/or may conform to the IS-1 standard when connecting a pacemaker/defibrillator to the electrodes 21-24.

FIG. 2A illustrates a side view of the connector assembly 50 of FIG. 1B. The connector assembly 50 includes a body segment 52 that is elongated, such as shaped in a tubular cross section or other cross section shaped to fit in a header receptacle. The body segment 52 is elongated along a longitudinal axis 58. The body segment 52 includes a header mating face 54 and a lead mating end 56. The header mating face 54 is loaded first into a receptacle in the header during an implant procedure. The body segment 52 is over-molded about various components, a portion of which are visible in FIG. 2. A connector pin 80 extends from the header mating face 54, while a plurality of termination pins 73-76 extend from the lead mating end 56. As explained herein, the body segment is over-molded about interior portions of the connector pin 80 and termination pins 73-76. Among other things, the over molding process reduces manufacturing steps, eliminates axial movement of the pins and provides a rigid interconnection between the various components, thereby maintaining predetermined tolerances and spacing between the components within the connector assembly 50. The connector pin 80 is fixed in a non-rotational position within the body segment.

The connector assembly 50 includes a plurality of ring contacts 64-66 that are spaced in an axially distributed manner along a length of the body segment 52. The ring contacts 64-66 are securely formed with the body segment 52 during the over molding process. The ring contacts 64-66 are separated from on another by seal zones 60-63 which represent portions of the body segment 52. The seal zones 60-63 facilitate electrical and physical separation and isolation between the ring contacts 64-66 and ensure no two ring contacts 64-65 engage a single contact within the header receptacle. In accordance with at least some embodiments, by securing the ring contacts 64-66 to the body segment 52 during the over molding process, a predetermined spacing is maintained, with a very small or narrow tolerance, for the ring contacts 64-66 relative to the connector pin 80. For example, predetermined spacings 81-83 may be defined as corresponding distances between the header mating face 54 of the body segment 52 and leading edges of the corresponding ring contacts 64-66. The spacings 81-83 are set such that each ring contact 64-66 will be aligned with an individual corresponding header contact within the receptacle of the header when the header mating face 54 of the body segment 52 engages or bottoms out with an interior wall of the header receptacle.

Once the over molding process is complete, the connector pin 80 and ring contacts 64-66 are held rigidly relative to one another in a manner that eliminates axial movement and that eliminates rotation (non-rotational relation). The ring contacts 64-66 extend about an exterior of the body segment 52 at predetermined positions along the body segment 52 and spaced a desired distance relative to the connector pin 80.

The body segment 52 also includes a lead interconnect region 68 configured to be received within and securely attached to the proximal end portion 16 of the lead body 12. The lead interconnect region 68 includes a support arm 77 and core post 78 that are formed integral with the body segment 52 and extend along the longitudinal axis 58 from the lead mating end 56. The lead interconnect region 68 also includes a plurality of support posts 72 positioned about the support arm 77 and extending from the lead mating end 56. The support posts 72 extend about and provide added support for the termination pins 73-76. The termination pins 73-76 extend in a common direction as the longitudinal axis 58 and are radially distributed outward from the longitudinal axis 58 and evenly spaced in a circumferential arrangement about the lead mating end 56.

FIG. 2B illustrates an end perspective view of the lead interconnect region 68 formed in accordance with an embodiment herein. The support arm 77 is formed with a non-rectangular, non-triangular cross-section. By way of example, the support arm 77 may have a fluted cross-section to provide channels 86 that form crimp pockets to receive crimp sleeves as explained hereafter. The channels 86 extend along and are spaced apart from the termination pins 73-76. The support arm 77 is formed with a channel 86 proximate to each of the termination pins 73-76. The channels 86 are separated from one another by ribs 88 that are located generally between adjacent termination pins 73-76 and extend in a common direction as the termination pins 73-76. FIG. 2B better illustrates the circumferential arrangement of the termination pins 73-76 that extend in a common direction as the longitudinal axis 58. The termination pins 73-76 are radially positioned outward from the longitudinal axis 58 and are spaced a select distance from one another to form a circumferential distribution about the lead mating end 56.

FIG. 2B also illustrates the support posts 72 to be tubular in shape and extend beyond an end 90 of the body segment 52. The support posts 72 provide added lateral support for the termination pins 73-76, such as during assembly and implant. The termination pins 73-76 are configured to be attached to proximal ends of corresponding ones of a plurality of conductors within the lead body 12 (as explained herein).

The core post 78 projects from the outer end of the support arm 77 and is centered along the longitudinal axis 58. The core post 78 may include one or more flared barbs 79 that is shaped and dimensioned to be frictionally secured within a core lumen within the proximal end portion 16 of the lead body 12. The barb 79 and core post 78 securer engage the distal end portion 16 to maintain the lead body 12 in an attached manner to the end of the connector assembly 50. The core post 78 securely engages the proximal end portion 16 to afford stability during assembly and afford a seal to prevent medical adhesive leakage during backfilling operations. It is recognized that additional fixation mechanisms may be used to secure the lead body 12 to the connector assembly 50, such as adhesives and other frictional features. For example, the support posts 72 may collectively define an outer envelope that is substantially similar to an interior dimension of a sheath of the lead body 12 such that the sheath at the distal end portion 16 frictionally engages the peripheral surfaces of the support posts 72.

FIG. 2C illustrates an end view of the connector assembly 50 from the lead making end 56. As shown in FIG. 2C, the support arm 77 includes a fluted cross-section having channels 86 that are positioned proximate to each of the termination pins 73-76. The spacing between the termination pins 73-76 and the corresponding channels 86 provide an area into which crimp sleeves are loaded onto the termination pins 73-76 to be coupled to the conductors within the lead body 12. Optionally, the support arm 77 may be removed entirely. Optionally, the support arm 77 may be provided with an alternative cross-section that affords sufficient space for the conductors to be terminated to the termination pins 73-76.

In accordance with at least one embodiment herein, a fluted geometry is provided on the support arm 77 with four channels or troughs that are positioned 90° from each other and off the pin axis by a select amount (e.g., 8°) to accommodate four evenly spaced distal termination pins. The troughs or channels 86 allow for placement of termination crimp sleeves within the space allowed by the interconnect region 68 (also referred to as a connector boot). The 8° offset of the centers of the channels 86 relative to a center of the termination pins 73-76 enables the crimp sleeves to be centered in the channels 86 to maximize clearance between components and facilitate assembly. In addition, the ribs 88 provide improved interaction with and locating of the interconnect region 68.

FIG. 2D illustrates a sectional view taken along line 2D-2D in FIG. 2C through the connector assembly 50 in accordance with an embodiment herein. The sectional view of FIG. 2D is taken through two of the termination pins 74-75 and through a center of the support arm 77. FIG. 2D illustrates the body segment 52 with the support arm 77 extending from the lead mating end 56. The body segment 52 over-molds the ring contacts 64-66, connector pin 80 and termination pins 73-76.

By way of example, the connector assembly 50 may represent an IS4 lead connector that allows connection of four co-radial cable connectors and no inner coil conductor. In certain cardiac resynchronization therapy (CRT) leads (and other passive fixation leads), connector pin rotation is not required. To reduce manufacturing process steps and eliminate axial pin movement (e.g., allow for the maximum allowable tolerance on linear contact and seal zone dimensions), the connector pin 80 is over-molded into the IS4 connector. The connector pin 80 (also referred to as a center conductor) may run a length of the body segment 52 and partially into the support arm 77 to provide structural rigidity and a means of terminating the connector pin 80. A collar 98 is present on the connector pin 80 distal of the connector pin to prevent the connector pin 80 from pulling out from the molded IS4 connector body when a tensile load is applied. In accordance with at least one embodiment, to maintain structural rigidity during molding while allowing for maximum molded material thickness between the center conductor and the rings for improved electrical isolation, a tapered center conductor design is utilized on the connector pin 80. The outer diameter of the connector pin 80 decreases from a maximum diameter at the proximal end to a minimum diameter at the distal end.

The termination pins 74 and 75 (as well as termination pins 73 and 76) are radially outwardly spaced from the longitudinal axis 58. The connector pin 80 includes a base section 92 that is rigidly secured during the molding process within the body segment 52. The connector pin 80 also includes an interconnect section 94 that extends beyond the header mating face 54 of the body segment 52. The interconnect section 94 of the connector pin 80 is sized, shaped and dimensioned to be securely received within (and conductively coupled to) a pin receptacle within the header 106 on the IMD 100. Additionally or alternatively, the interconnect section 94 may be sized, shaped and dimensioned to be securely received within (and conductively coupled to) a pin receptacle within an external device 600.

As illustrated in FIG. 2D, the connector pin 80 is aligned with and extends along the longitudinal axis 58 of the body segment 52. The connector pin 80 includes a lumen 87 that extends along the entire length of the connector pin 80. The support arm 77 and core post 78 also include a lumen 89 that aligns with the lumen 87. The lumens 87 and 89 align with a core lumen extending along a length of the lead body. By way of example, the lumen 87, 89 and lumen of the lead body may receive a guide wire or stylet or other tool in connection with implanting or explanting the lead. The connector pin 80 includes an inner end 94 that is terminated within one of the support arm 77 and body segment 52. The inner end 94 of the connector pin 80 is spaced apart from and does not physically or electrically touch conductors within the lead body 12. Instead, the support arm 77 and core post 78 project beyond the inner end 94.

The barb feature 79 on the post 78 provides stability during assembly and creates a seal to prevent medical adhesive leakage into the inner lumen of the lead body. The post 78 and barb feature 79 are sized to be accepted into the inner diameter of the load body. An interference fit between the inner diameter of the lead body and post 78 and barb feature 79 improves stability during assembly and affects a seal to prevent leakage of medical adhesive to the inner diameter of the lead. In this embodiment, a tapered "barb" feature is utilized to increase the amount of interference between components over a small region. Optionally, the barb feature 79 may be omitted.

In the illustrated embodiment, the inner end 94 of the connector pin 80 extends into the support arm 77 to provide added mechanical strength to the support arm 77. Optionally, the inner end 94 may be terminated within the body segment 52 or extend into the core post 78. The base section 92 of the connector pin 80 may be constructed in a tapered manner with a larger diameter proximate to the header mating face 54 and a smaller diameter proximate to the lead mating end 56. The taper in the base section 92 may be a constant gradual taper, a series of stepped tapers or otherwise. As one example, the taper in the base section 92 facilitates maintaining a fixed axial relation between the connector pin 80 and the body segment 52 during insertion and connection to a header 106. The flared collar 98 located within the body segment 52 facilitates maintaining a fixed axial relation between the connector pin 80 and the body segment 52, such as during manufacturing, assembly, implantation, operation and otherwise. For example, during attachment of the connector assembly 50 to a header 106, an axial loading pressure or force may be experienced on one or both of the connector pin 80 and body segment 52. The adhesive and structural feature interconnection between the connector pin 80 and body segment 52 prevent axial movement there between when exposed to axial loading or tensile (puffing) pressures and forces.

A collar coupler 150 securely and electrically couples a proximal end of the termination pin 74 to the ring contact 64. A collar coupler 152 securely and electrically couples a proximal end of the termination pin 75 to the ring contact 66. While not illustrated in FIG. 2D, separate collar couplers securely and electrically couple the termination pins 73 and 72 to the ring contact 65 and the connector pin 80.

Figure 2E:
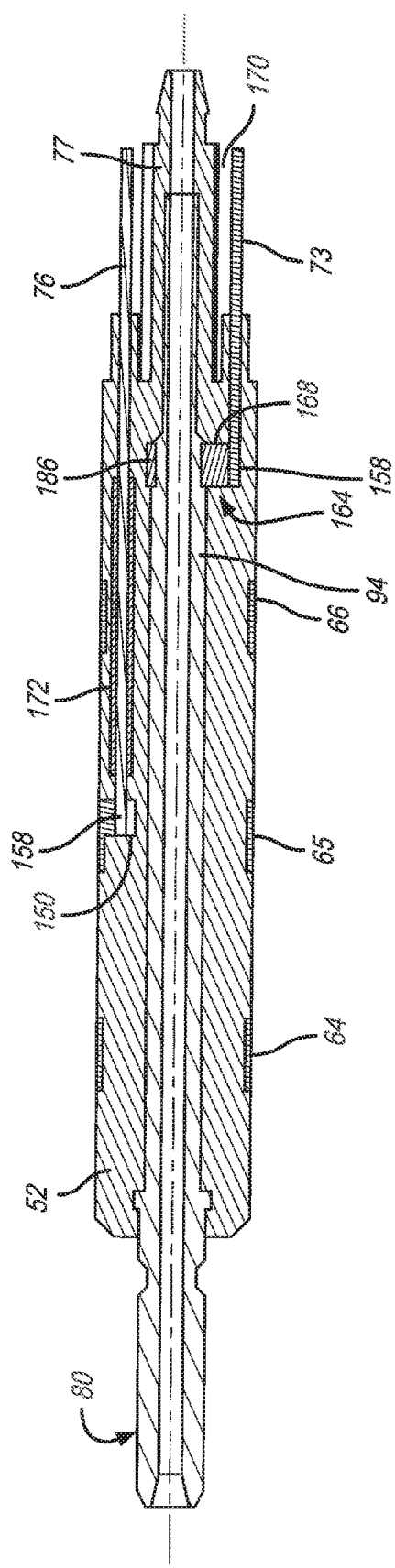
FIG. 2E illustrates a sectional view taken along line 2E-2E in FIG. 2C through the connector assembly.

FIG. 2E illustrates a sectional view taken along line 2E-2E in FIG. 2C through the connector assembly 50 in accordance with an embodiment herein. The sectional view of FIG. 2E is taken through the two termination pins 73, 76 that are oriented at a right angle to the termination pins 74, 75 through the section line 2D-2D. FIG. 2E illustrates the body segment 52 with the support arm 77. The body segment 52 includes the ring contacts 64-66 and connector pin 80.

In the cross-sectional view of FIG. 2E, a support collar 164 is illustrated with the base segment 166 extending about the interconnect section 94 of the connector pin 80. The support collar 164 also includes a standoff section 168 that securely receives and retains the base stem 158 of the termination pin 73. As illustrated in FIG. 2E, the termination pin 73 represents a straight pin 10 where the base stem 158 is held in the standoff section 168 a predetermined distance spaced apart from the support arm 77 to afford a gap 170 there between. The termination pin 76 extends a greater length than the termination pin 73 such that the base stem 158 of the termination pin 76 extends to the intermediate ring contact 65. A collar 150 joins the base stem 158 of the termination pin 76 to the ring contact 65.

The termination pins 74 and 75 (as well as termination pins 73 and 76) are offset radially from the longitudinal axis 58. The connector pin 80 includes a base section 92 that is rigidly secured during the molding process within the body segment 52. The connector pin 80 also includes an interconnect section 94 that extends beyond the header mating face 54 of the body segment 52. The interconnect section 94 of the connector pin 80 is sized, shaped and dimensioned to be securely received within (and conductively coupled to) a pin receptacle within the header 106 on the IMD 100. Additionally or alternatively, the interconnect section 94 may be sized, shaped and dimensioned to be securely received within (and conductively coupled to) a pin receptacle within an external device 600.

Figure 3A:
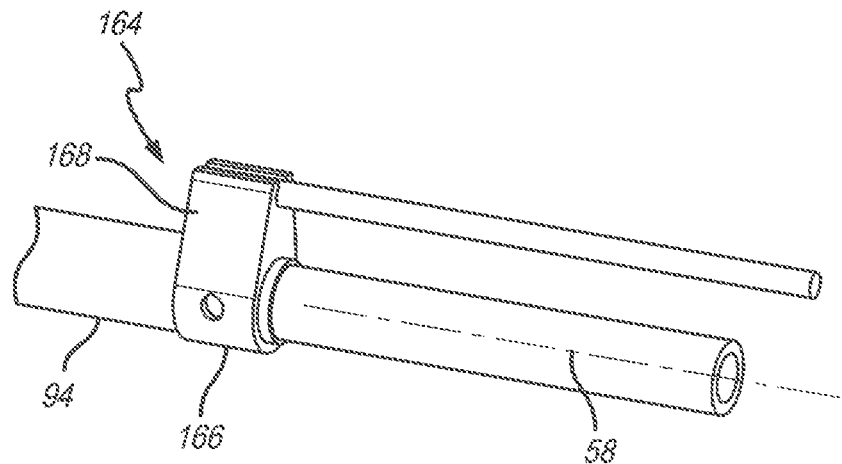
FIG. 3A illustrates a perspective view of the interconnection area between the connector pin and the corresponding termination pin formed in accordance with an embodiment herein.

FIG. 3A illustrates a perspective view of interconnection area between the connector pin 80 and the corresponding termination pin 73 in accordance with an embodiment. The support collar 164 is configured to maintain a secure and conductive connection between the interconnect section 94 and the termination pin 73. The support collar 164 includes a base segment 166 and a standoff section 168 formed integral with one another. The base segment 166 extends about the interconnect section 94, while the standoff section 168 projects radially outward from the longitudinal axis 58. The standoff section 158 is positioned to enclose the base stem 158 thereby providing added mechanical support to the interconnection between the termination pin 73 and the interconnect section 94.

Figure 3B:
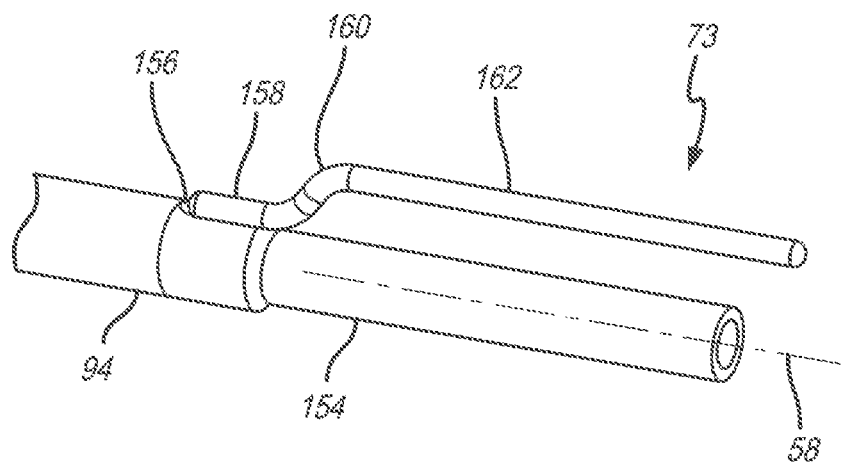
FIG. 3B illustrates a perspective view of an interconnection region between the connector pin and the corresponding termination pin formed in accordance with an embodiment herein.

To accommodate termination of multiple (four) termination crimp sleeve and cable assemblies, an offset termination method (as illustrated in FIGS. 3A and 3B) is used to connect the fourth termination pin 74 to the center connector pin 80. The offset termination provides the electrical connection from the lead connector pin 80 to the distal tip electrode. Two designs for this attachment method are illustrated, namely the "outrigger" concept (FIG. 3A) and the "bent pin" concept (FIG. 3B). The outrigger concept utilizes a collar-like component which is welded to the connector pin 80. The fourth termination pin 74 is welded to the outrigger component prior to over-molding. The bent pin concept (FIG. 3B) utilizes a distal termination pin 74 that is formed with two bends and welded directly to the center connector pin 80 prior to molding.

FIG. 3B illustrates a perspective view of an interconnection area between the connector pin 80 and the corresponding termination pin 73 in accordance with an embodiment. In FIG. 3B, a portion of the interconnect section 94 is illustrated along with a tapered step 154 between different diameter portions of the interconnect section 94. The interconnect section 94 also includes a recess 166 extending in the direction of the longitudinal axis 58 and located along the perimeter of the interconnect section 94. The termination pin 73 includes a base stem 158, an offset section 160 and a main leg 162 formed integral with one another and shaped, relative to one another, in a curved relation. The base stem 158 fits into the recess 156 to form a physical and electrical connection between the termination pin 73 and connector body 80. The base stem 158 includes an outer end that abuts against a terminating end of the recess 158 to prevent and resist axial movement of the termination pin 73 relative to the interconnect section 94, such as during assembly with the lead body 12. The offset section 160 is curved to extend in a generally radial direction outward from the interconnect section 94 in a non-parallel orientation relative to the longitudinal axis 58. As illustrated in FIG. 3B, the offset section 160 extends at an acute angle relative to the longitudinal axis 58.

Optionally, the offset section 160 may extend perpendicular or in another direction relative to the longitudinal axis 58. The main leg 162 extends at an obtuse angle relative to the offset section 160 such that the main leg 162 extends generally parallel (or at a very small acute angle relative) to the longitudinal axis 58. The main leg 162 is radially displaced from the interconnect section 94 to provide a working space there between, as well as room for the support arm 77.

Figure 4:
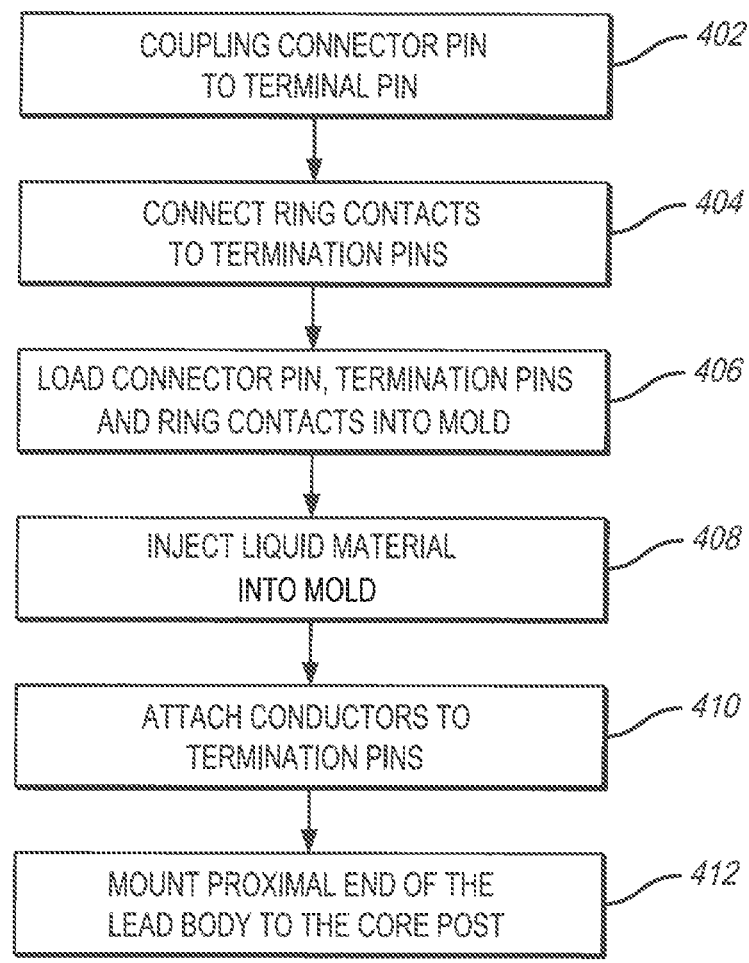
FIG. 4 illustrates a flowchart for a method of manufacture for a lead assembly in accordance with embodiments herein.

FIG. 4 illustrates a flowchart for a method of manufacture for a lead assembly in accordance with embodiments herein. The method provides a lead connector, beginning at 402 by coupling a connector pin and a first termination pin to one another through a collar coupler such that the connector pin and first termination pin are in an axially offset alignment with one another. At 404, the ring contacts 64-66 are attached to corresponding termination pins 74-77 through collar couplers 150. Optionally, also at 404, the insulated tubing sections 172 may be placed over the termination pins 74-77.

Figure 8:
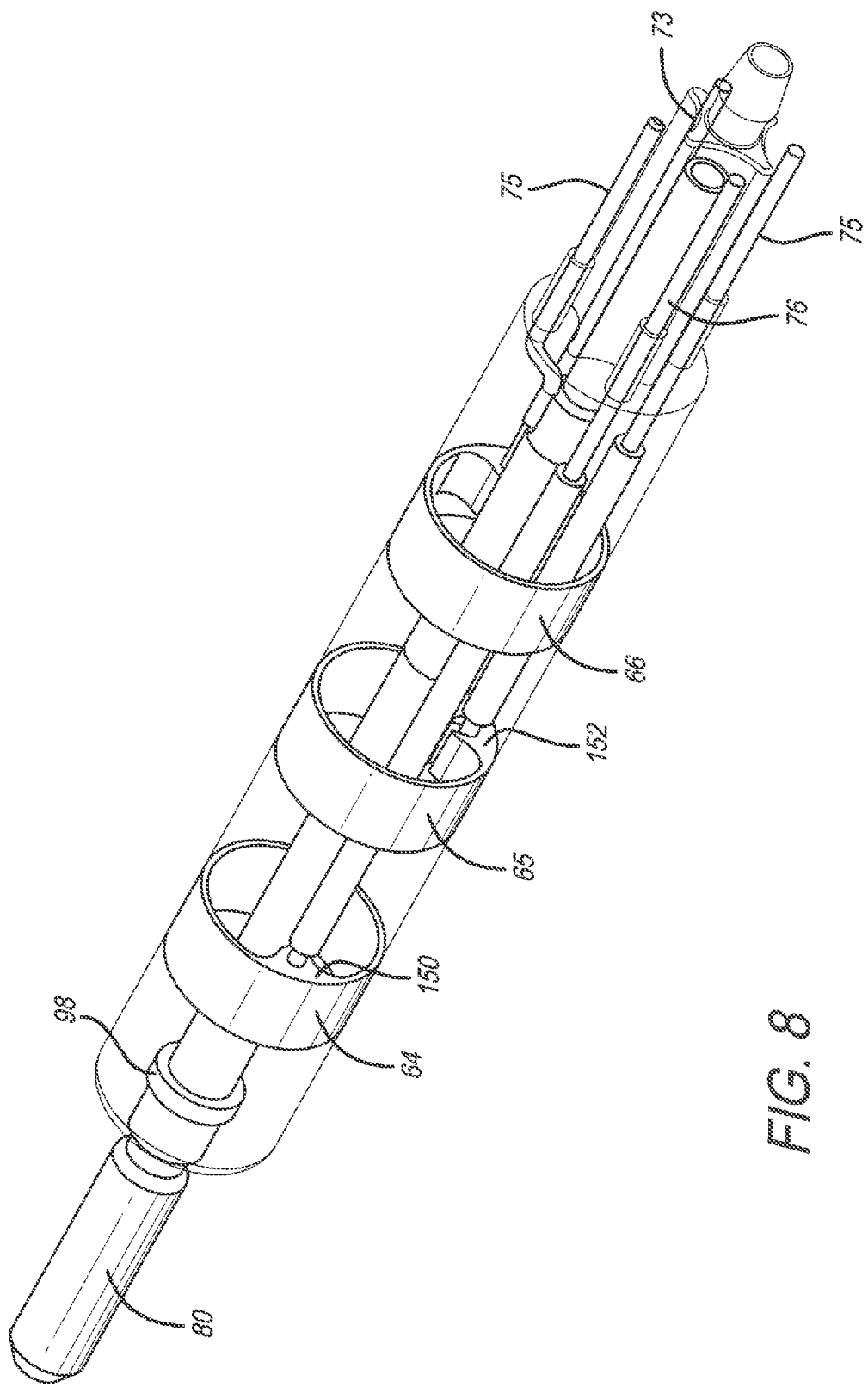
FIG. 8 illustrates the components as loaded in a mold in accordance with an embodiment herein.

At 406, the connector pin, termination pins, ring contacts and any other appropriate structures described herein or otherwise known are loaded into a mold at predetermined positions relative to one another corresponding to the final positions and spacing to be maintained in the final connector assembly 50. For example, FIG. 8 illustrates the components as loaded in a mold.

At 408, the material forming the body segment is injection molded while in a liquid state, at an elevated temperature and under high pressure, such that the liquefied material fills the appropriate areas within the mold and securely engages each of the other components loaded into the mold. Once the body segment cools and solidifies, the connector assembly is removed from the mold. Optionally, finishing operations may be performed, such as (but not limited) to removing excess material from surfaces of the ring contacts and elsewhere.

Figure 5:
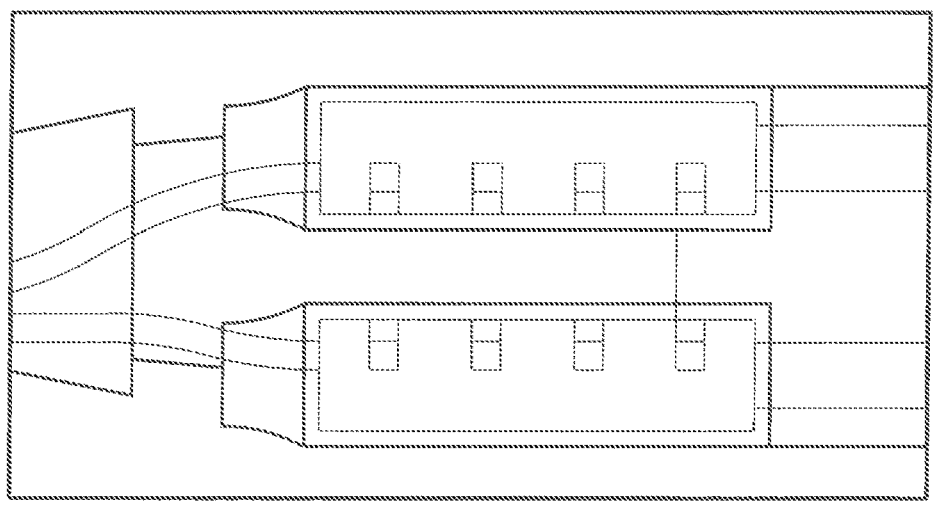
FIG. 5 illustrates proximal ends of the conductors when loaded into crimping sleeves that are then loaded over the termination pins in accordance with an embodiment herein.

At 410 conductors within the lead body are securely and electrically attached to the termination pins. For example, as shown in FIG. 5, proximal ends of the conductors may be loaded into crimped sleeve that are then loaded over the termination pins in the areas proximate the channels along the sides of the support arm. Exterior surfaces of the crimped elements are collapsed in a crimping manner to securely affix the conductors and the termination pins within the crimped sleeves.

At 412, a proximal end of the lead body is attached to the lead mating end of the connector assembly. A plurality of electrodes are disposed along the lead body, where separate conductors are joined to each of the electrodes. For example, the lead body may include a lumen that frictionally receives the core post. Additionally or alternatively, the proximal end of the lead body may be secured to other features on the lead mating end of the connector assembly. When the lead body is fully loaded onto the lead mating end of the connector assembly, the outer shroud of the lead body securely abuts against the lead mating end to form a tight seal with the body segment.

Figure 6:
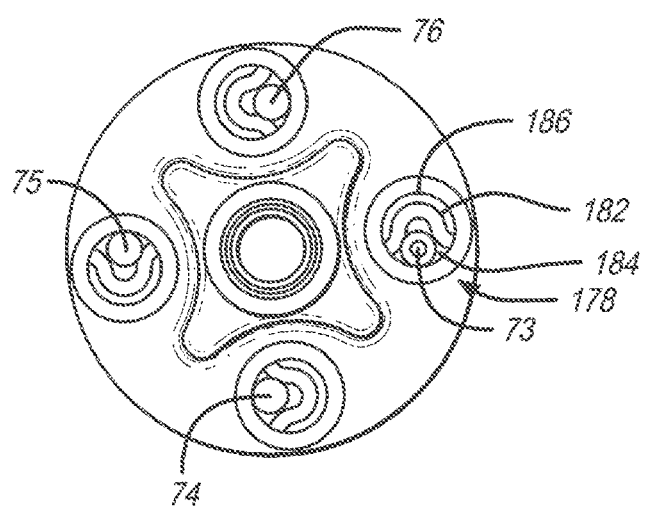
FIG. 6 illustrates an end view of the connector assembly from the lead mating end after the crimping sleeves have been installed to secure the conductors to the termination pins in accordance with an embodiment herein.

FIG. 6 illustrates an end view of the connector assembly 50 from the lead mating end 56 after the crimping sleeves have been installed to secure the conductors to the termination pins 73-76. End views of crimping sleeves 178 are illustrated. Each crimping sleeve 178 includes a wire reception area 182 and a pin reception area 184. The conductors 186 are inserted into the wire reception area 182, while the pins 73-76 are inserted into the pin reception areas 184. When the components are aligned in a desired manner, one or more deflection portions 180 located along a length of each crimping sleeve 178 are crimped or deflected inward to frictionally and securely engage the corresponding pin 73 and conductors 186.

In FIG. 6, the support arm 77 includes a fluted cross-section having channels 86 that are positioned proximate to each of the termination pins 73-76. The spacing between the termination pins 73 to 76 and the corresponding channels 86 provide an area into which crimp sleeves are loaded onto the termination pins 73-76 to be coupled to the conductors within the lead body 12. Optionally, the support arm 77 may be removed entirely. Optionally, the support arm 77 may be provided with an alternative cross-section that affords sufficient space for the conductors to be terminated to the termination pin 73-76.

Figure 7:
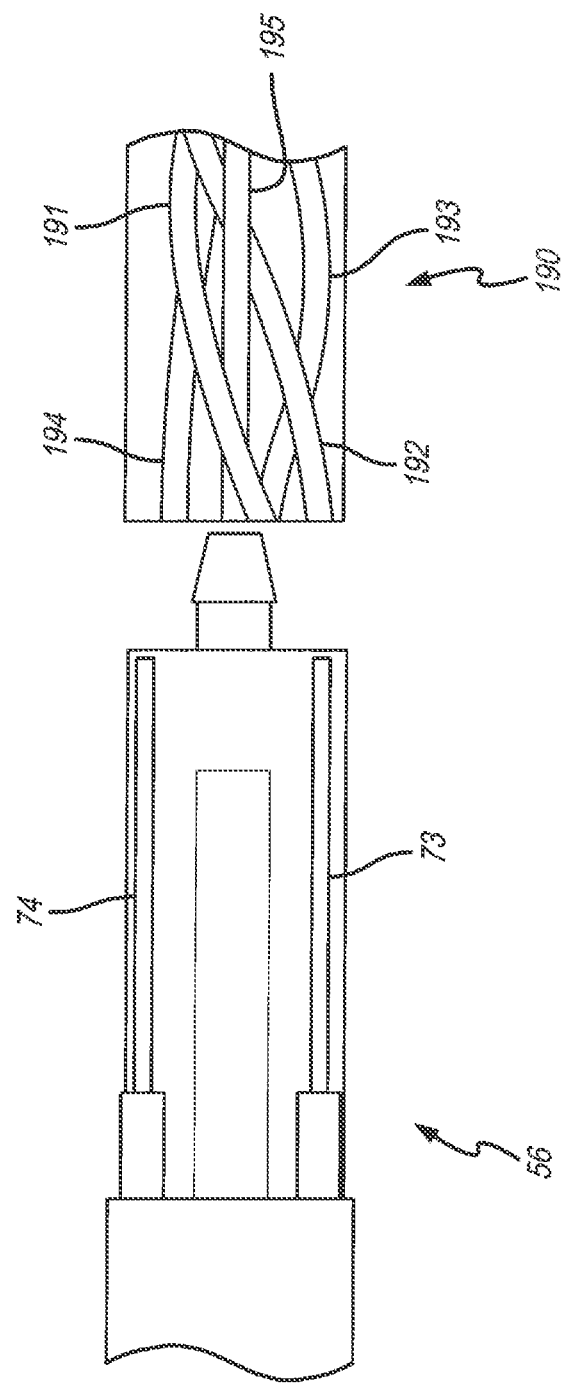
FIG. 7 illustrates a side perspective view of the lead mating end of the connector assembly and the proximal portion of the lead body in accordance with an embodiment herein.

FIG. 7 illustrates a side perspective view of the lead mating end 56 of the connector assembly 50 and the proximal portion 190 of the lead body 12. The lead body includes multiple conductors 191-194. The conductors 191-194 wrap around in a spiral manner about a core lumen 195 within the lead body 12. As explained above, the core post 78 is securely affixed within an open end of the lumen 195 and the proximal ends of the conductors 191-194 are secured to the termination pins 73-76.

Optionally, embodiments herein may be implemented with passive or active fixation leads. For example, the connector assembly 50 may be implemented with an active fixation lead where the connector pin 80 is not needed to rotate to cause rotation of the fixation element. For example, the fixation element may be driven in other manners.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A method of manufacturing a lead assembly, comprising:
   providing a lead connector by:
   coupling a connector pin to a first termination pin through a collar coupler such that the connector pin and first termination pin are in an axially offset alignment with one another; and
   over molding a body segment about the connector pin, the first termination pin and the collar coupler, the body segment being elongated along a longitudinal axis and extending between a header mating face and a lead mating end, the connector pin positioned along the longitudinal axis and extending from the header mating face, the first termination pin positioned axially offset from the longitudinal axis and extending from the lead mating end;
   attaching the lead connector to a proximal end portion of a lead body having a plurality of electrodes disposed along the lead body, the lead body including a plurality of cable conductors; and
   joining the first termination pin to a proximal end of a first conductor from the plurality of cable conductors.

2. The method of claim 1, further comprising affixing the connector pin within the body segment in a non-rotational manner, and electrically coupling the connector pin to the first conductor by attaching the first conductor to the first termination pin through a crimp sleeve, the cable conductors winding in a spiral manner about a length of the lead body.

3. The method of claim 1, further comprising
   coupling a plurality of termination pins to ring contacts;
   loading the plurality of termination pins, the ring contacts, the first termination pin, and the connector pin into an injection mold; and
   over molding the plurality of termination pins, the ring contacts, the first termination pin, and the connector pin such that the plurality of termination pins project from the lead mating end and the ring contacts extend circumferentially about an exterior of the body segment at predetermined positions spaced along the body segment.

4. The method of claim 1, further comprising spacing the ring contacts along a length of the body segment by a spacing relative to the header mating face of the body segment.

5. The method of claim 1, wherein the plurality of termination pins and the first termination pin extend in a common direction as the longitudinal axis and are radially distributed outward from the longitudinal axis in a circumferential arrangement about the lead mating end.

6. The method of claim 1, wherein the connector pin includes a base section that is tapered along a length thereof and is rigidly secured during molding within the body segment.

7. The method of claim 1, wherein the body segment includes a lead interconnect region extending from the lead mating end, the lead interconnect region having a fluted cross-section to form crimp pockets, the conductors being joined through crimp sleeves to corresponding termination pins in the crimp pockets.

8. The method of claim 1, wherein the body segment further comprises a support arm and core post projecting from lead mating end and centered along the longitudinal axis, the core post including a flared barb, the core post and barb shaped and dimensioned to be frictionally secured within a core lumen within a proximal end portion of the lead body.

* * * * *